United States Patent
Chen et al.

(10) Patent No.: US 9,840,563 B2
(45) Date of Patent: Dec. 12, 2017

(54) METHOD FOR TREATING AND/OR PREVENTING ATRIAL FIBRILLATION

(71) Applicant: Chang Gung Memorial Hospital, Linkou, Taoyuan (TW)

(72) Inventors: Wei-Jan Chen, Taoyuan (TW);
Yung-Hsinn Yeh, Taoyuan (TW);
Shang-Hung Chang, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 0 days.

(21) Appl. No.: 14/876,231

(22) Filed: Oct. 6, 2015

(65) Prior Publication Data

US 2016/0215057 A1     Jul. 28, 2016

(30) Foreign Application Priority Data

Jan. 23, 2015     (TW) .............................. 104102357 A

(51) Int. Cl.
| | | |
|---|---|---|
| *A61K 39/395* | (2006.01) | |
| *C07K 16/28* | (2006.01) | |
| *A61K 45/06* | (2006.01) | |
| *A61K 39/00* | (2006.01) | |

(52) U.S. Cl.
CPC .......... *C07K 16/2884* (2013.01); *A61K 45/06* (2013.01); *A61K 2039/505* (2013.01); *C07K 2317/76* (2013.01)

(58) Field of Classification Search
None
See application file for complete search history.

(56) References Cited

U.S. PATENT DOCUMENTS

2012/0309960 A1*   12/2012   Quan .................. C07D 487/08
                                                            540/456
2013/0224108 A1   8/2013   Da Cruz et al.

FOREIGN PATENT DOCUMENTS

WO    WO-2013/063498 A1    5/2013

OTHER PUBLICATIONS

Finet et al., Cardiol Clin 27(1): 1-12 (2008).*
Muller-Sieburg et al., Blood Cells, Molecules, and Diseases 26(4): 291-302 (2000).*
Chang et al "Blocking CD44 Attenuates Atrial Fibrilation and Fibrosis via the STAT3 Pathway" ESC Congress, Barcelona, 2014.

* cited by examiner

*Primary Examiner* — Phillip Gambel
(74) *Attorney, Agent, or Firm* — Cesari and McKenna, LLP

(57) ABSTRACT

Disclosed herein is a method for treating and/or preventing atrial fibrillation in a subject, comprising administering to the subject a pharmaceutical composition comprising an anti-CD44 neutralizing antibody or an antigen binding portion thereof which specifically binds to the amino-terminal domain of CD44. The anti-CD44 neutralizing antibody is a monoclonal antibody. The pharmaceutical composition further includes a pharmaceutically acceptable carrier.

3 Claims, 4 Drawing Sheets

METHOD FOR TREATING AND/OR PREVENTING ATRIAL FIBRILLATION

CROSS-REFERENCE TO RELATED APPLICATIONS

This application claims priority of Taiwanese Application No. 104102357, filed on Jan. 23, 2015.

BACKGROUND

Field of the Invention

The disclosure relates to a method for treating and/or preventing atrial fibrillation in a subject, which uses an anti-CD44 neutralizing antibody or an antigen binding portion thereof that specifically binds to the amino-terminal domain of CD44.

Background Information

Atrial fibrillation (AF), a most common cardiac arrhythmia, is characterized by rapid and irregular heartbeat caused by abnormal sinus rhythm in atrium. The incidence of atrial fibrillation increases with age.

Decrease in action potential duration due to reduced protein expression of L-type calcium channel (LCC) and reduced LCC current is involved in the pathogenesis of atrial fibrillation. Reduction in LCC current is a response that leads to potential protection of atrial myocytes against intracallular $Ca^{2+}$ overload. The resultant decrease in action potential duration gives rise to shortening of the atrial effective refractory period. Such shortening of the atrial effective refractory period subsequently slows intra-atrial conduction and induces intra-atrial reentry, thus contributing to the development of atrial fibrillation.

Although there is no immediate risk of death, long-term atrial fibrillation may cause palpitation, cardiomyopathy, loss of effective atrial contraction, decrease of cardiac output, and even severe complications such as angina cordis and stroke.

Recent therapeutic approaches for atrial fibrillation include:

(1) rhythm control, which is performed by electric cardioversion, catheter ablation or a drug to restore normal sinus rhythm so as to achieve synchronized contraction of the atrium and ventricle and so as to further result in normal cardiac output [examples of suitable drugs include quinidine (a class I antiarrhythmia agent) and sotalol (a class III antiarrhythmia agent)]; and (2) rate control, which is performed using a drug to lower the ventricular heart rate to approximately a normal level (about 60 to 100 bpm) without changing sinus rhythm [examples of suitable drugs include a β-blocker (e.g., atenolol) and a calcium channel blocker (e.g., diltiazem)].

However, the therapeutic effects achieved by the above-mentioned approaches are limited. Moreover, the above-mentioned approaches cannot effectively prevent the development of complications and may lead to serious side effects (e.g., heart failure). Therefore, there is a need in the art to develop drugs that are effective in the treatment of atrial fibrillation and that induce no undesired side effect.

CD44 is a transmembrane glycoprotein that participates in many cellular processes including the regulation of growth, survival, differentiation and motility. CD44 is expressed on the surface of most mammalian cells, which include normal cells such as hematopoietic cells, keratinocytes, chondrocytes, epithelial cells, endothelial cells, neural cells, etc., as well as cancer cells such as colon cancer cells, breast cancer cells, etc.

CD44 is encoded by a single and highly conserved gene, and various isoforms thereof having a molecular weight ranging from 80 to 200 kD are generated by alternative splicing of mRNA. CD44 isoforms can be classified into a standard isoform (referred to as CD44s or CD44H) and variant isoforms (referred to as CD44v) based on the existence of a peptide fragment encoded by variable exons. Each CD44 isoform has an amino-terminal domain, which is encoded by exons 1 to 5 and which is highly conserved among mammalian species. The amino-terminal domain is located outside of the cell membrane and regulates cell-cell and environment-cell interactions by binding with different components of an extracellular matrix (ECM), e.g., hyaluronic acid, collagen, laminin, fibronectin, etc. The amino-terminal domain also regulates transcription by binding with transcription factors through internalization and nuclear translocation.

Much research has been dedicated to the use of an anti-CD44 antibody in disease treatment and pharmaceutical field. For example, US 2013/0224108 A1 discloses a method of treating a head and neck squamous cell carcinoma (HN-SCC, which expresses CD44) in a mammal. The method includes administering to the mammal an isolated monoclonal anti-CD44 antibody or an antigen-binding fragment thereof in an amount that effectively results in a reduction of said mammal's tumor burden. The antibody and antigen-binding fragment thereof specifically binds to an epitope within the amino-terminal domain of the extracellular region of CD44 and thus has specificity to multiple isoforms of CD44 expressed in human. The epitope comprises an amino acid sequence of AFDGPITITIV (SEQ ID NO:1).

WO 2013/063498 A1 discloses a method for treating or preventing a hematological malignancy in a subject, comprising administering to a subject in need thereof a therapeutically effective amount of an antibody that specifically binds to CD44. Particularly, the antibody can specifically bind to various CD44 isoforms (including CD44s and CD44v). The hematological malignancy is refractory to chemotherapy and/or biotherapy, and may be B-cell chronic lymphocytic leukemia (CLL).

Through research, the Inventors surprisingly found that anti-CD44 neutralizing antibodies effectively increase the protein expression of LCC of atrial myocytes with tachy-pacing-induced atrial fibrillation, and decrease the incidence of atrial fibrillation in mice. Therefore, anti-CD44 neutralizing antibodies are expected to be useful in treating and/or preventing atrial fibrillation.

SUMMARY

Therefore, according to an aspect of the disclosure, a method for treating and/or preventing atrial fibrillation in a subject includes administering to the subject a pharmaceutical composition comprising an anti-CD44 neutralizing antibody or an antigen binding portion thereof which specifically binds to amino-terminal domain of CD44.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
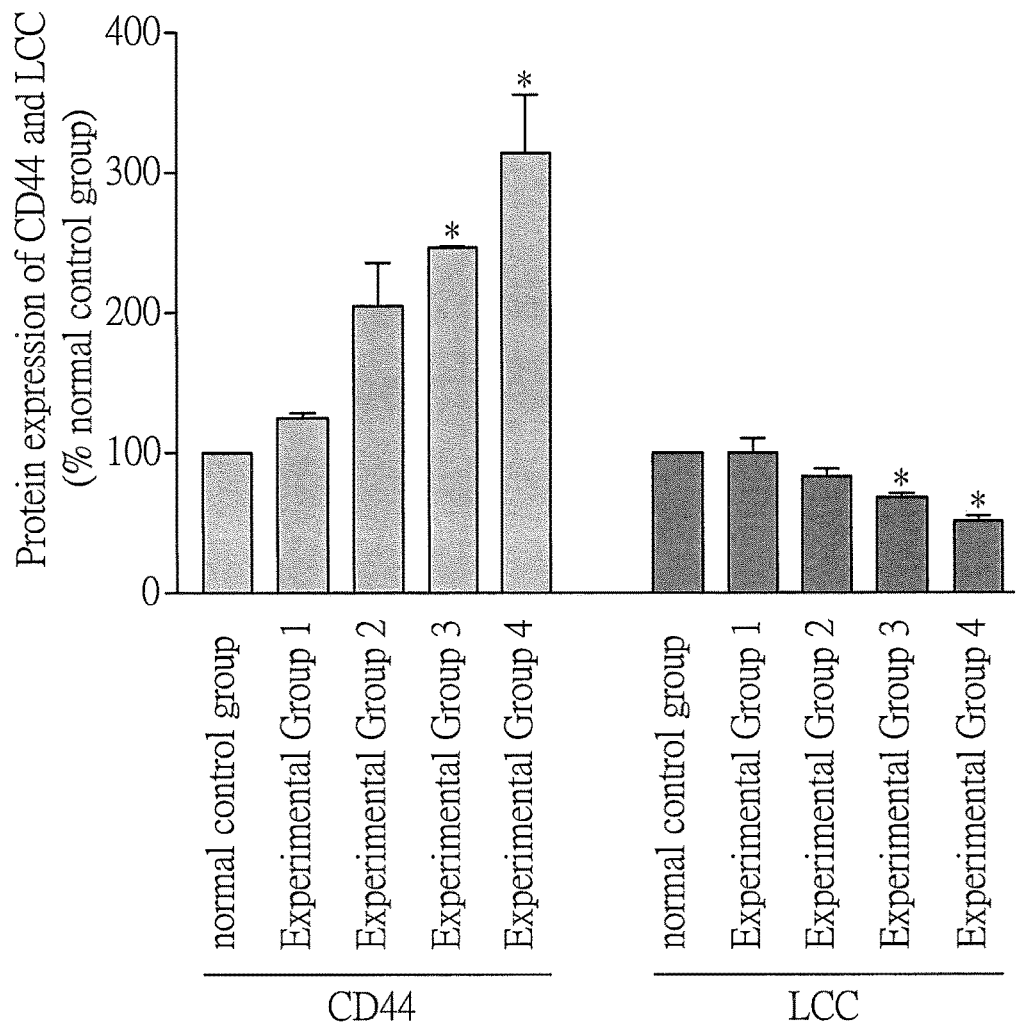
FIG. 1 shows protein expressions of CD44 and L-type calcium channel (LCC) of HL-1 cells in a normal control group and Experimental Groups 1 to 4 after electric field stimulation, wherein the cells in Experimental Groups 1 to 4 were respectively subjected to electric field stimulation for 2, 6, 12 and 24 hrs), the cells in the normal control group did not receive electric field stimulation, and "*" represents p<0.05 as compared with the normal control group.

It is to be understood that, if any prior art publication is referred to herein, such reference does not constitute an admission that the publication forms a part of the common general knowledge in the art, in Taiwan or any other country.

For the purpose of this specification, it should be clearly understood that the word "comprising" means "including but not limited to", and that the word "comprise" has a corresponding meaning.

Unless otherwise defined, all technical and scientific terms used herein have the meaning as commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

In developing drugs for treating and/or preventing atrial fibrillation, the Inventors surprisingly found that anti-CD44 neutralizing antibodies have potential to treat and/or prevent atrial fibrillation. In particular, by virtue of the experimental results, the Inventors found that: anti-CD44 neutralizing antibodies which specifically bind to the amino-terminal domain of CD44 effectively increase protein expression of L-type calcium channel (LCC) of HL-1 cells with tachypacing-induced atrial fibrillation and decrease the incidence of atrial fibrillation in mice.

Accordingly, the disclosure provides a method for treating and/or preventing atrial fibrillation in a subject, comprising administering to the subject a pharmaceutical composition comprising an anti-CD44 neutralizing antibody or an antigen binding portion thereof which specifically binds to amino-terminal domain of CD44.

As used herein, the term "treating" or "treatment" refers to reducing, alleviating, ameliorating, relieving, or controlling one or more clinical signs of a disease or disorder, and lowering, stopping, or reversing the progression of severity regarding the condition or symptom being treated.

As used herein, the term "antibody" is used in the broadest sense, and is intended to encompass monoclonal antibodies (including chimeric antibodies and humanized antibodies), polyclonal antibodies, multispecific antibodies (e.g., bispecific antibodies), antibody fragments (including $F_{ab}$, $F_{ab'}$, $F_{(ab')2}$ and $F_v$ fragments) and synthetic polypeptides carrying one or more complementarity determining region (CDR) or CDR-derived sequences and exhibiting desired biological activities. The antibodies of the present disclosure can be of any class (e.g., IgG, IgE, IgM, IgD and IgA), or any subclass thereof (e.g., $IgG_1$, $IgG_2$, $IgG_{2a}$, $IgG_3$, $IgG_4$, $IgA_1$ and $IgA_2$).

As used herein, the term "anti-CD44 neutralizing antibody" refers to any antibody capable of specifically binding to CD44 and substantially inhibiting or eliminating the biological activity of CD44.

Preferably, the anti-CD44 neutralizing antibody is an $IgG_1$ monoclonal antibody.

As used herein, the term "antigen binding portion" refers to one or more fragments of the anti-CD44 neutralizing antibody, which have the antigen binding ability of the antibody and can neutralize the biologically activity of CD44.

According to the disclosure, the anti-CD44 neutralizing antibody or antigen binding portion thereof can be prepared according to techniques well known and routinely used by those skilled in the art. In this aspect, reference may be made to, e.g., Kohler and Milstein (1975), Nature, 256:495-497, Kohler and Milstein (1976), European J. Immunol., 6:511-519, Huse et al. (1989), Science 246:1275-1281, Clackson et al. (1991), Nature, 352:624-628, Marks et al. (1991), J. Mol. Biol., 222:581-597, Borrabeck (1995), Antibody Engineering, 2nd ed. Oxford University Press, U.S. Pat. No. 4,816,567, and U.S. Pat. No. 7,816,500 B2.

Preferably, the anti-CD44 neutralizing antibody can be prepared from a hybridoma cell line capable of producing anti-CD44 monoclonal antibodies according to techniques well known and routinely used by those skilled in the art. The hybridoma cell line may be obtained from global depository institutions.

According to the disclosure, the anti-CD44 neutralizing antibody can be of a type well known and routinely used by those skilled in the art, which includes, but is not limited to, anti-CD44 monoclonal antibody KM201, anti-CD44 monoclonal antibody KM81, anti-CD44 monoclonal antibody KM114, anti-CD44 monoclonal antibody KM703, anti-CD44 monoclonal antibody SACK-1, anti-CD44 monoclonal antibody FW11-9-2, anti-CD44 monoclonal antibody FW11-10-3, anti-CD44 monoclonal antibody FW11-24-17-36, anti-CD44 monoclonal antibody LYK-1, anti-CD44 monoclonal antibody LYK-5, anti-CD44 monoclonal antibody LYK-7, anti-CD44 monoclonal antibody LYK-8, anti- CD44 monoclonal antibody LYK-9, anti-CD44 monoclonal antibody LYK-12 and anti-CD44 monoclonal antibody LYK-16.

According to the disclosure, the hybridoma cell line may be purchased from American Type Culture Collection (ATCC), and includes, e.g., ATCC® TIB-240™, ATCC® TIB-241™, ATCC® TIB-242™, ATCC® CRL-1896™, ATCC® PTA-9008™, ATCC® HB-256™, ATCC® HB-257™, ATCC® HB-258™, ATCC® HB-306™, ATCC® HB-310™, ATCC® HB-311™, ATCC® HB-312™, ATCC® HB-313™, ATCC® HB-316™ and ATCC® HB-319™.

In an embodiment of the disclosure, the anti-CD44 neutralizing antibody is anti-CD44 monoclonal neutralizing antibody KM201 produced from hybridoma cell line ATCC® TIB-240™.

Alternatively, the anti-CD44 neutralizing antibody or antigen binding portion thereof can be a commercially available product, which includes, but is not limited to, anti-CD44 monoclonal antibody A3D8 (Sigma-Aldrich, Cat. No. C7923), anti-CD44 monoclonal antibody 1E1 (Sigma-Aldrich, Cat. No. SAB1402714), anti-CD44 monoclonal antibody IM7 (Sigma-Aldrich, Cat. Nos. SAB4700188 and SAB4700189), anti-CD44 monoclonal antibody MEM-85 (Sigma-Aldrich, Cat. Nos. SAB4700179, SAB4700180, SAB4700181 and SAB4700183), anti-CD44 monoclonal antibody MEM-263 (Sigma-Aldrich, Cat. Nos. SAB4700184, SAB4700185, SAB4700186 and SAB4700187) and, anti-CD44 polyclonal antibodies (Sigma-Aldrich, Cat. No. HPA005785, SAB1405590 and GW22755).

The pharmaceutical composition according to the present disclosure may be administered via one of the following parenteral routes: intraperitoneal injection, subcutaneous injection, intramuscular injection and intravenous injection. In an embodiment of the present disclosure, the pharmaceutical composition is formulated into a dosage form for intraperitoneal injection.

For the parenteral routes, the pharmaceutical composition according to the present disclosure is formulated into an injection using technology well known to those skilled in the art, e.g., a sterile aqueous solution or a dispersion.

According to the disclosure, the pharmaceutical composition may additionally comprise a pharmaceutically acceptable carrier widely employed in the art of drug-manufacturing. For instance, the pharmaceutically acceptable carrier may include one or more of the following agents: solvents (such as sterile water), buffers (such as phosphate buffered saline (PBS), Ringer's solution and Hank's solution), emulsifiers, suspending agents, pH adjusting agents, stabilizing agents, chelating agents, preservatives, diluents, absorption delaying agents, liposomes, and the like. The choice and amount of these pharmaceutically acceptable carriers are within the expertise of those skilled in the art.

According to the disclosure, the pharmaceutical composition may be used in combination with one or more of the cardiovascular drugs selected from the group consisting of anticoagulants (such as heparin and enoxaparin), antiarrhythmia agents (such as amiodarone and lidocaine), and platelet glycoprotein IIb/IIIa receptor antagonists (such as abciximab, eptifibatide and tirofiban).

According to the disclosure, the dosage and administration intervals of the pharmaceutical composition of the present disclosure may depend on the following factors: the severity of the disease to be treated, the administration route, and the age, physical condition and response of the subject to be treated. In general, the anti-CD44 neutralizing antibody or antigen binding portion thereof may be administered at a weekly dosage of from 10 µg/kg body weight to 500 µg/kg body weight of the subject in a single dose or in multiple doses.

The present disclosure will be further described by way of the following examples. However, it should be understood that the following examples are intended solely for the purpose of illustration and should not be construed as limiting the disclosure in practice.

EXAMPLES

Experimental Materials:

1. Source and Culture of Mouse Atrial Myocyte Cell Line HL-1:

Mouse atrial myocyte cell line HL-1 used in the following examples was provided by Dr. William C. Claycomb at Louisiana State University.

HL-1 cells were seeded in a Petri dish containing Claycomb medium (JRH Biosciences, Sigma-Aldrich) supplemented with 10% fetal bovine serum (FBS)(JRH Biosciences, Sigma-Aldrich) and $10^4$ µg/mL streptomycin (Life Technologies), followed by cultivation in an incubator with culture conditions set at 37° C. and 5% $CO_2$. Medium change was performed every three days. When about 80% confluence was reached, the medium was removed, and followed by washing the cells two times with PBS. Trypsin-EDTA was added so as to detach the cells from the bottom of the Petri dish. Subsequently, a fresh medium was added to neutralize activity of trypsin and the cells were sufficiently dispersed in medium by virtue of repeated aspiration with a pipette. Then, the resultant cell suspension was dispensed to new Petri dishes, followed by cultivation in an incubator with culture conditions set at 37° C. and 5% $CO_2$.

2. Experimental Animals:

Male MHC-TGFcys$^{33}$ser mice (4 to 8 weeks old, a body weight of about 15 to 25 g) used in the following examples were provided by Dr. Loren J. Field at Indiana University. All of the experimental animals were kept in an animal room with an independent air conditioning system under the following laboratory conditions: a temperature of 23±1° C., a relative humidity of 50±5%, and a 12 hour light/12 hour dark cycle. Furthermore, food and water were provided ad libitum. All experimental procedures involving the experimental animals were approved by Institutional Animal Care and Use Committee of Linkou Chang Gung Memorial Hospital and were performed in accordance with the NIH (National Institutes of Health) Guide for the Care and Use of Laboratory Animals.

General Experimental Procedures:

1. Analysis of Protein Samples:

Protein samples were subjected to sodium dodecyl sulfate-polyacrylamide gel electrophoresis (SDS-PAGE) analysis and Western Blotting analysis according to techniques well known and routinely used by those skilled in the art. The instruments and reagents used were as follows.

(1) SDS-PAGE analysis was performed using a vertical electrophoresis cell (Bio-Rad).

(2) Protein transfer was performed using a protein transfer kit (Bio-Rad) and a polyvinylidene difluoride (PVDF) membrane (PerkinElmer).

(3) In Western Blotting analysis, primary and secondary antibodies used for detecting each protein are shown in Table 1.

TABLE 1

| Protein | Primary Antibody | Secondary Antibody |
| --- | --- | --- |
| CD44 | Rabbit anti-CD44 polyclonal antibody (Abcam, Cat. No. ab41478) | Goat anti-rabbit IgG-horseradish peroxidase (HRP) antibody (Thermo, Cat. No. PI-31460) |
| L-type calcium channel (LCC) | Rabbit anti-LCC α1C subunit polyclonal antibody (Santa Cruz, Cat. No. sc-25686) | Goat anti-rabbit IgG-HRP antibody |
| Tubulin | Mouse anti-tubulin monoclonal antibody (Santa Cruz, Cat. No. sc-32293) | Goat anti-mouse IgG-HRP antibody (Thermo, Cat. No. PI-31430) |

(4) Chemiluminescence staining was performed using 4CN PLUS Chromogenic Substrate (Perkin Elmer), and Western Lightning™ (Perkin Elmer) was used to detect signal.

2. Statistical Analysis:

In the following examples, experiments for each group were repeated 5 times. The experimental data are expressed as "mean±standard error of the mean (SEM)." All the data were analyzed using one-way analysis of variance (one-way ANOVA) so as to evaluate the difference between the groups. $p<0.05$ represents statistical significance.

Example 1. Effect of Atrial Fibrillation on Protein Expressions of CD44 and LCC

In this example, the in vitro test was performed using HL-1 cells with tachypacing-induced atrial fibrillation, and the effect of atrial fibrillation on protein expressions of CD44 and LCC was evaluated. Tachypacing was performed essentially in accordance with the procedures described in Yeh Y. H. et al. (2011), *Cardiovascular Research*, 91:62-70.

Experimental Procedures:

Eight groups of HL-1 cells (including a normal control group and seven experimental groups referred to as Experimental Groups 1 to 7) were provided. Then, the cells of each group were added to a 4-well rectangular culture dish (Nunclon®)($1\times10^6$ cells/well) containing 3 mL Claycomb medium supplemented with 10% FBS and $10^4$ μg/mL streptomycin and then incubated in an incubator (37° C., 5% $CO_2$) for 24 hours.

Subsequently, the medium in each group was replaced with fresh Claycomb medium supplemented with 10% FBS and $10^4$ μg/mL streptomycin. Then, Experimental Groups 1 to 7 were subjected to electric field stimulation (i.e., tachypacing) at a field strength of 1.5 V/cm using C-Pace EP culture pacer/C-Dish™ system (IonOptix), and operation conditions for Experimental Groups 1 to 7 are shown in Table 2. The normal control group was not subjected to electric field stimulation.

TABLE 2

| Group | Frequency (Hz) | Voltage intensity (V) | Stimulus duration (ms) | Total stimulus time (hr) |
| --- | --- | --- | --- | --- |
| Experimental Group 1 | 4 | 40 | 10 | 2 |
| Experimental Group 2 | 4 | 40 | 10 | 6 |
| Experimental Group 3 | 4 | 40 | 10 | 12 |
| Experimental Group 4 | 4 | 40 | 10 | 24 |
| Experimental Group 5 | 1 | 40 | 10 | 24 |
| Experimental Group 6 | 2 | 40 | 10 | 24 |
| Experimental Group 7 | 4 | 40 | 10 | 24 |

Afterwards, the medium in each group was removed and 300 μL of a lysis buffer (containing 50 mM HEPES, 250 mM NaCl, 5 mM EDTA, and 0.1% NP40) was added, followed by mixing homogeneously. The resultant cell mixture was placed in a microcentrifuge tube, followed by shaking for 5 minutes. Then, the microcentrifuge tube containing the cell mixture was placed on ice for 30 minutes, followed by going through centrifugation at 4° C. and 15,000 rpm for 15 minutes to obtain a supernatant serving as a protein sample.

The protein sample in each group was subjected to a Western Blotting analysis for CD44 and LCC expressions along the lines as described in the previous "1. Analysis of protein samples" section of "General Experimental Procedures", with tubulin being used as an internal control.

The image thus obtained was analyzed using Image Gauge software, such that the protein expression level could be semi-quantitatively calculated from the protein band. The protein expression level was then normalized against the corresponding protein expression level of tubulin. The normalized protein expression level in the normal control group was defined as 100%, and the percentage of the protein expression in each group relative to the normal control group (represented as % normal control group) was calculated.

Figure 2:
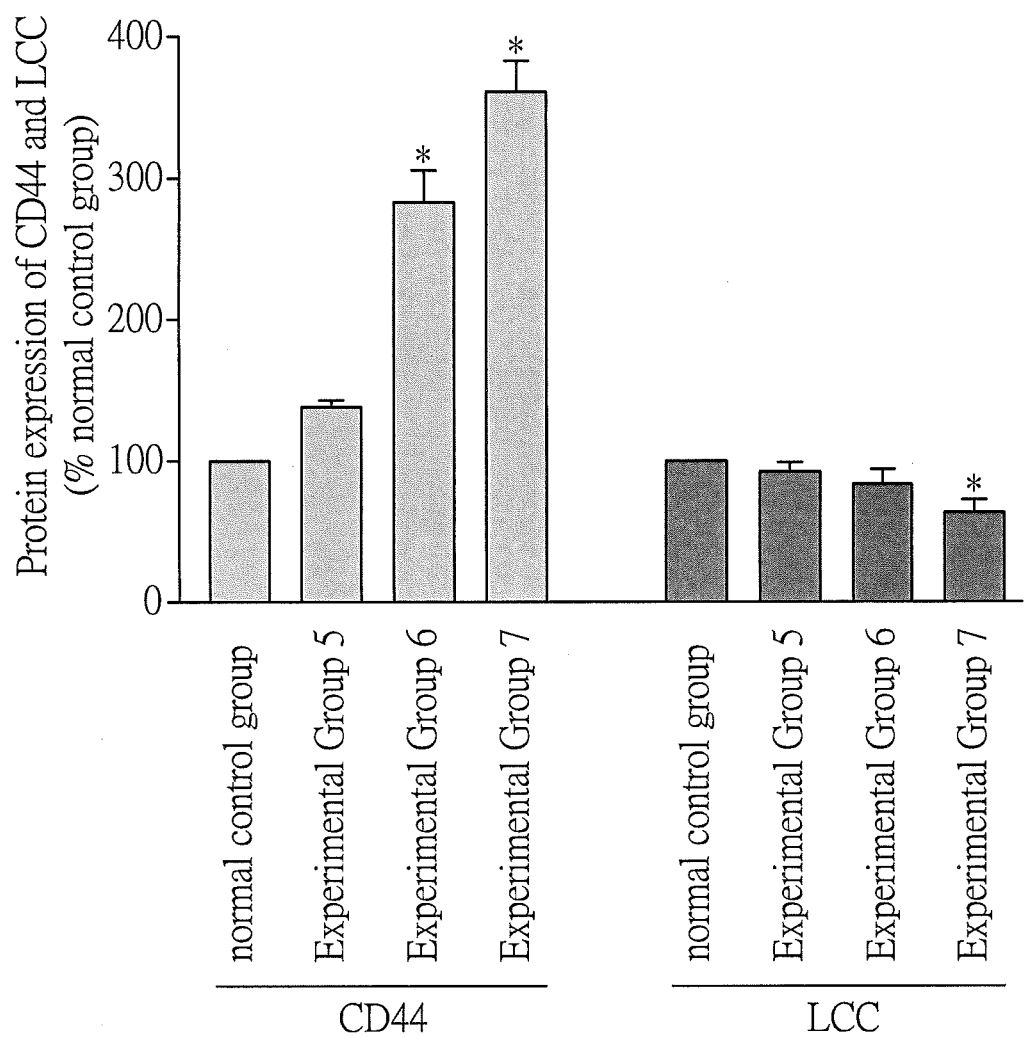
FIG. 2 shows protein expressions of CD44 and LCC of HL-1 cells in a normal control group and Experimental Groups 5 to 7 after electric field stimulation, wherein the cells in Experimental Groups 5 to 7 were respectively subjected to electric field stimulation under different frequencies (i.e., 1, 2 and 4 Hz), the cells in the normal control group did not receive electric field stimulation, and "*" represents p<0.05 as compared with the normal control group.

Results:

The protein expressions of CD44 and LCC of HL-1 cells subjected to electric field stimulation for different total stimulus time and different frequencies are shown in FIGS. 1 and 2.

It can be seen from FIG. 1 that, the protein expression of CD44 in each of Experimental Groups 1 to 4 is higher than that of the normal control group, and increases with an increase of total stimulus time of electric field stimulation. Further, the protein expression of LCC in each of Experimental Groups 1 to 4 is lower than that of the normal control group, and decreases with an increase of total stimulus time of electric field stimulation.

FIG. 2 reveals that the protein expression of CD44 in each of Experimental Groups 5 to 7 is higher as compared with that of the normal control group, and increases with an increase of frequency of field stimulation. Further, the protein expression level of LCC in each of Experimental Groups 5 to 7 is lower as compared with that of the normal control group, and decreases with an increase of frequency of field stimulation.

The experimental results suggest that CD44 may be associated with the decrease in the protein expression of LCC of HL-1 cells with tachypacing-induced atrial fibrillation. Therefore, the effect of anti-CD44 neutralizing antibody on the decrease in the protein expression of LCC of HL-1 cells with tachypacing-induced atrial fibrillation is further evaluated.

Example 2. Effect of Anti-CD44 Neutralizing Antibody on the Decrease in the Protein Expression of LCC of HL-1 Cells with Tachypacing-Induced Atrial Fibrillation In this example, in vitro test was performed using HL-1 cells with tachypacing-induced atrial fibrillation, and an anti-CD44 monoclonal neutralizing antibody which specifically binds to the amino-terminal domain of CD44 (KM201, which recognizes an epitope very close to the hyaluronic acid-biding region in the amino-terminal domain of CD44) was employed so as to evaluate the effect of anti-CD44 neutralizing antibody on the protein expression of LCC.

Experimental Procedures:

Four groups of HL-1 cells (including two IgG antibody groups referred to as IgG Antibody Groups 1 and 2 and two anti-CD44 antibody groups referred to as Anti-CD44 Antibody Groups 1 and 2) were provided. Then, the cells of each group were added to a 4-well rectangular culture dish ($1\times10^6$ cells/well) containing 3 mL Claycomb medium supplemented with 10% FBS and $10^4$ μg/mL streptomycin. Thereafter, a suitable amount of an IgG antibody (R187, produced by hybridoma cell line ATCC® CRL-1912™) was added into each of IgG Antibody Groups 1 and 2 so that each of IgG Antibody Groups 1 and 2 had a final concentration of IgG antibody of 25 μg/mL, and a suitable amount of an anti-CD44 monoclonal neutralizing antibody (KM201, produced by hybridoma cell line ATCC® TIB-240™) was added into each of Anti-CD44 Antibody Groups 1 and 2 so that each of Anti-CD44 Antibody Groups 1 and 2 had a final concentration of anti-CD44 neutralizing antibody of 25 μg/mL.

After incubation in an incubator (37° C., 5% $CO_2$) for 24 hours, the medium in each group was replaced with fresh Claycomb medium supplemented with 10% FBS and $10^4$ μg/mL streptomycin. Then, IgG Antibody Group 2 and Anti-CD44 Antibody Group 2 were subjected to electric field stimulation at field strength of 1.5 V/cm using C-Pace EP culture pacer/C-Dish™ system, and operation conditions were shown in Table 3. IgG Antibody Group 1 and Anti-CD44 Antibody Group 1 were not subjected to electric field stimulation.

TABLE 3

| Frequency (Hz) | Voltage intensity (V) | Stimulus duration (ms) | Total stimulus time (hr) |
| --- | --- | --- | --- |
| 4 | 40 | 10 | 24 |

Afterwards, the medium in each group was removed and 300 μL of lysis buffer was added, followed by mixing homogeneously. The resultant cell mixture was placed in a microcentrifuge tube, followed by shaking for 5 minutes. Then, the microcentrifuge tube containing the cell mixture was placed on ice for 30 minutes, followed by going through centrifugation at 4° C. and 15,000 rpm for 15 minutes to obtain a supernatant serving as a protein sample.

The protein sample in each group was subjected to a Western Blotting analysis for LCC expression along the lines as described in the previous "1. Analysis of protein samples" section of "General Experimental Procedures", with tubulin being used as an internal control.

The image thus obtained was analyzed using Image Gauge software, such that the protein expression level could be semi-quantitatively calculated from the protein band. The protein expression level was then normalized against the corresponding protein expression level of tubulin. The normalized protein expression level in IgG Antibody Group 1 was defined as 100%, and the percentage of the protein expression in each group relative to IgG Antibody Group 1 (represented as % IgG Antibody Group 1) was calculated.

Figure 3:
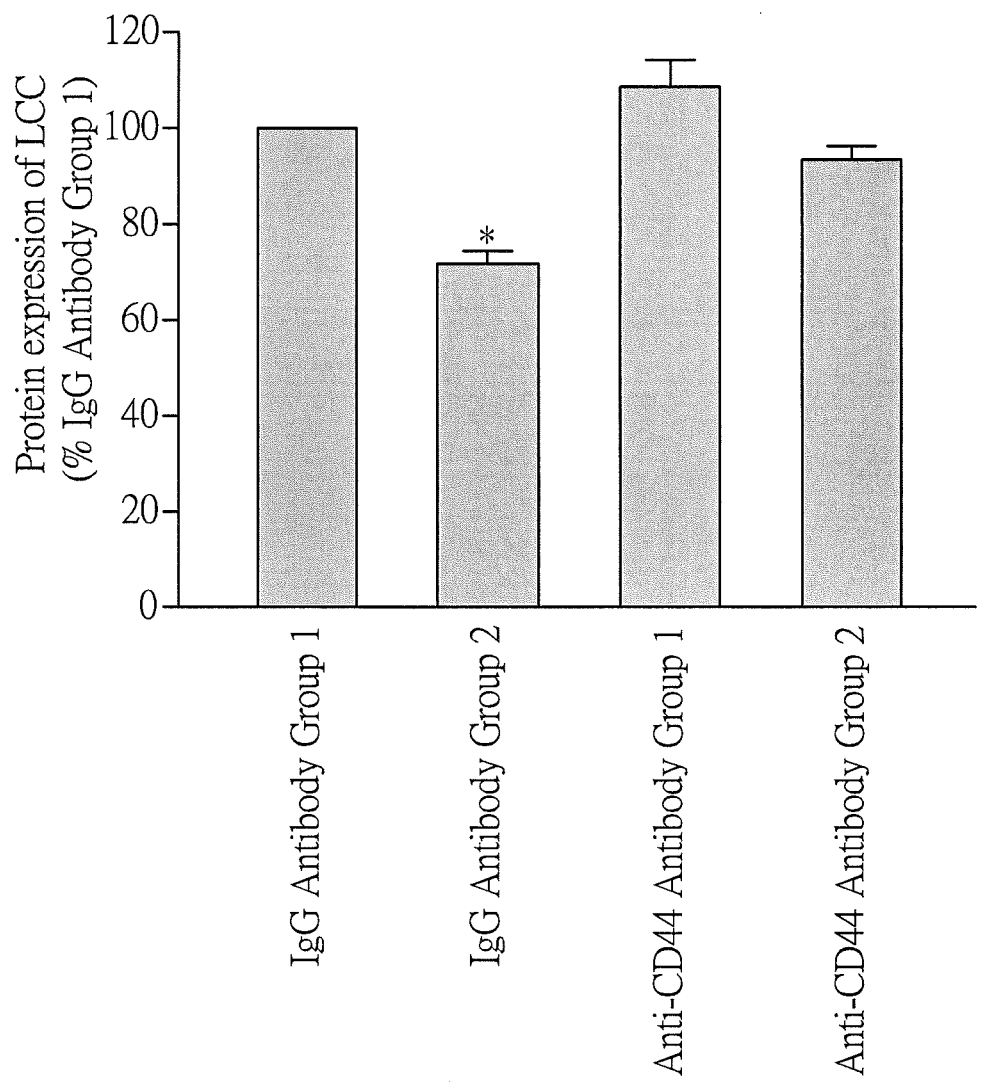
FIG. 3 shows protein expression of LCC of HL-1 cells in IgG Antibody Groups 1 and 2 and Anti-CD44 Antibody Groups 1 and 2 after electric field stimulation, wherein the cells in IgG Antibody Group 1 were treated with IgG antibody, the cells in IgG Antibody Group 2 were treated with IgG antibody and subjected to electric field stimulation, the cells in Anti-CD44 Antibody Group 1 were treated with anti-CD44 monoclonal neutralizing antibody, the cells in Anti-CD44 Antibody Group 2 were treated with anti-CD44 monoclonal neutralizing antibody and subjected to electric field stimulation, and "*" represents p<0.05 as compared with IgG Antibody Group 1.

Results:

The protein expression of LCC of IgG Antibody Groups 1 and 2 and Anti-CD44 Antibody Groups 1 and 2 are shown in FIG. 3. It can be seen from FIG. 3 that there is statistical significance between the protein expression of LCC in IgG Antibody Group 2 and that in IgG Antibody Group 1. On the contrary, there is no statistical significance between the protein expression of LCC in Anti-CD44 Antibody Group 2 and that in Anti-CD44 Antibody Group 1. The experimental results reveal that the anti-CD44 neutralizing antibody is effective in preventing the decrease in the protein expression of LCC of HL-1 cells with tachypacing-induced atrial fibrillation. Therefore, the anti-CD44 neutralizing antibody is deemed to have potential to alleviate atrial fibrillation.

Example 3. Evaluation for In Vivo Anti-Atrial Fibrillation Effect of Anti-CD44 Neutralizing Antibody In this example, the induction and detection of atrial fibrillation in mice were performed essentially in accordance with the procedures described in Verheule S. et al. (2004), *Circulation Research*, 94:1458-1465 so as to evaluate the effect of anti-CD44 neutralizing antibody on the incidence of atrial fibrillation.

Experimental Procedures:

The male MHC-TGFcys[33]ser mice were randomly divided into three groups: a control group, IgG Antibody Group, and Anti-CD44 Antibody Group (n=6 for each group). Saline was administered to the mice in the control group via intraperitoneal injection at a dose of 500 μL/mouse, IgG antibody (in 500 μL saline) and anti-CD44 neutralizing antibody (in 500 μL saline) were respectively administered to the mice in IgG Antibody Group and Anti-CD44 Antibody Group via intraperitoneal injection at a dose of 300 μg/mouse. The mice in each group was subjected to the once-a-week administration for eight weeks.

After eight weeks of administration, mice in each group were anesthetized using pentobarbital. Then, mice in IgG Antibody Group and Anti-CD44 Antibody Group were subjected to programmed electrical stimulation using stimulus isolation unit (St. Jude Medical) connected with transesophageal stimulation electrodes (Supreme™ Electrophysiology Catheters, St. Jude Medical). There were two series of burst pacing in the programmed electrical stimulation, and each series contained eleven burst pacings. The operation conditions are shown in Table 4. During the programmed electrical stimulation, atrial rhythm was detected using electrodes of stimulus isolation unit. A mouse is considered to have atrial fibrillation if at least two seconds of rapid irregular atrial rhythms are detected. The mice in the control group were not subjected to the programmed electrical stimulation, but atrial rhythm thereof was detected. Afterwards, the incidence of atrial fibrillation in each group was calculated based on the following equation.

Incidence of atrial fibrillation (%)=the number of mice having atrial fibrillation/the total number of mice*100%

Figure 4:
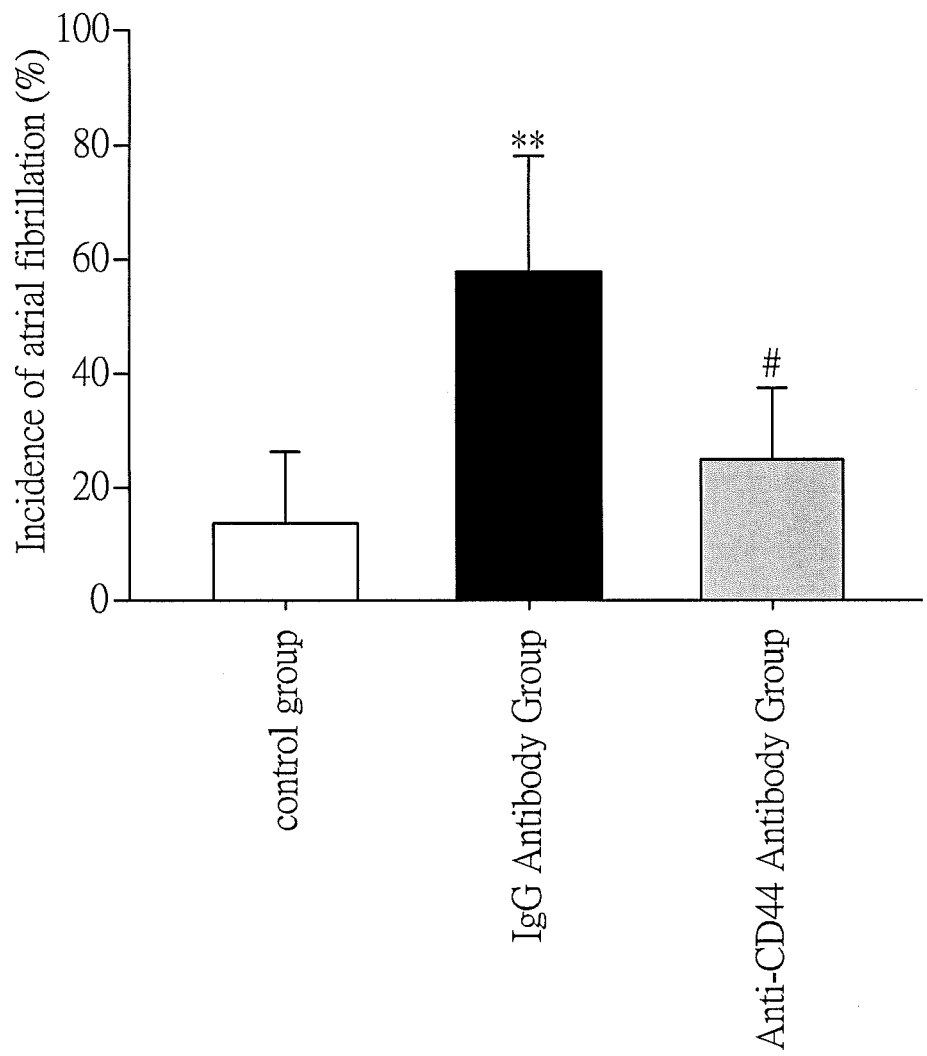
FIG. 4 shows the incidence of atrial fibrillation of mice in a control group, IgG Antibody Group, and Anti-CD44 Antibody Group, wherein the mice in IgG Antibody Group were injected with IgG antibody for eight weeks and subjected to programmed electrical stimulation, the mice in Anti-CD44 Antibody Group were injected with anti-CD44 monoclonal neutralizing antibody for eight weeks and subjected to programmed electrical stimulation, the mice in the control group were injected with saline for eight weeks but were not subjected to programmed electrical stimulation, "**" represents p<0.01 as compared with the control group, and "#" represents p<0.05 as compared with the IgG antibody group.

Results:

The incidence of atrial fibrillation of the control group, IgG Antibody Group, and Anti-CD44 Antibody Group are shown in FIG. 4. It can be seen from FIG. 4 that the incidence of atrial fibrillation of Anti-CD44 Antibody Group is significantly lower than that of IgG Antibody Group, and is even close to that of the control group. The experimental results reveal that the anti-CD44 neutralizing antibody is effective in alleviating atrial fibrillation.

In view of the foregoing, anti-CD44 neutralizing antibodies are effective in treating and/or preventing atrial fibrillation by preventing a decrease in the protein expression of LCC.

All the patents and references cited in this specification are incorporated herein in their entirety as reference. When there is conflict, the detailed descriptions in this case, including the definitions, would prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: epitope

<400> SEQUENCE: 1

Ala Phe Asp Gly Pro Ile Thr Ile Thr Ile Val
1               5                   10

TABLE 4

|  | Stimulus amplitude | 1.5 × diastolic capture threshold |
| --- | --- | --- |
| Stimulus duration (ms) |  | 1 |
| burst pacing duration (s) |  | 2 |
| cycle length (CL) of each burst pacing (ms) | 1th | 40 |
|  | 2nd | 38 |
|  | 3rd | 36 |
|  | 4th | 34 |
|  | 5th | 32 |
|  | 6th | 30 |
|  | 7th | 28 |
|  | 8th | 26 |
|  | 9th | 24 |
|  | 10th | 22 |
|  | 11th | 20 |

The invention claimed is:

1. A method for treating atrial fibrillation in a subject, comprising administering to the subject a pharmaceutical composition comprising an anti-CD44 neutralizing antibody or an antigen binding portion thereof which specifically binds to the amino-terminal domain of CD44, wherein the anti-CD44 neutralizing antibody is monoclonal antibody KM201 produced by hybridoma cell line American Type Culture Collection TIB-240.

2. The method of claim 1, wherein the pharmaceutical composition further comprises a pharmaceutically acceptable carrier.

3. The method of claim 1, wherein the pharmaceutical composition is in a dosage form for parenteral administration.

* * * * *